US005269954A

United States Patent [19]

Germanaud et al.

[11] Patent Number: 5,269,954

[45] Date of Patent: Dec. 14, 1993

[54] NITROGENOUS ADDITIVES WITH AN ANTIOXIDANT ACTION AND LUBRICATING COMPOSITIONS CONTAINING THE SAID ADDITIVES

[75] Inventors: Laurent Germanaud, Valentin le Fayet; Patrick Azorin, Mornant; Patrick Turello, Francheville, all of France

[73] Assignee: Elf France, Courbevoie, France

[21] Appl. No.: 799,700

[22] Filed: Nov. 25, 1991

Related U.S. Application Data

[63] Continuation of Ser. No. 445,392, Dec. 4, 1989, abandoned.

[30] Foreign Application Priority Data

Dec. 5, 1988 [FR] France ................................ 88 15913

[51] Int. Cl.[5] ................. C10M 135/36; C07D 279/36; C07D 279/18; C07D 279/24

[52] U.S. Cl. ..................................... 252/47; 252/47.5; 252/402; 544/31; 544/37; 544/38; 544/41

[58] Field of Search ........................ 252/47, 47.5, 402; 544/31, 37, 38, 41

[56] References Cited

U.S. PATENT DOCUMENTS

| | | | |
|---|---|---|---|
| 2,528,092 | 10/1950 | Smith et al. | 252/47.5 |
| 2,595,215 | 5/1952 | Charpentier | 544/41 |
| 2,781,318 | 2/1957 | Cyphers | 252/47 |
| 2,815,343 | 12/1957 | Horsley et al. | 544/38 |
| 2,976,286 | 3/1961 | Schindler | 544/41 |
| 3,238,199 | 3/1966 | Berger et al. | 544/41 |
| 3,344,068 | 9/1967 | Waight et al. | 252/47 |
| 3,347,857 | 10/1967 | Paquette | 544/41 |
| 3,376,224 | 4/1968 | Elliott et al. | 252/402 |
| 3,389,124 | 6/1968 | Sparks | 252/47 |
| 3,431,270 | 3/1969 | Paquette | 544/41 |
| 3,454,598 | 7/1969 | Yale et al. | 544/41 |
| 3,803,140 | 4/1974 | Cook et al. | 252/402 |
| 4,072,619 | 2/1978 | Williams et al. | 252/47 |
| 4,565,834 | 1/1986 | Buysch et al. | 544/38 |
| 4,785,095 | 11/1988 | Salomon | 544/31 |
| 4,798,684 | 1/1989 | Salomon | 252/402 |
| 4,877,824 | 10/1989 | Evans | 252/47 |
| 4,915,858 | 4/1990 | Salomon | 252/402 |
| 5,024,774 | 6/1991 | Salomon | 252/47 |
| 5,035,817 | 7/1991 | Salomon | 252/47 |
| 5,051,198 | 9/1991 | Salomon | 252/47 |
| 5,157,118 | 10/1992 | Salomon | 252/47.5 |
| 5,178,783 | 1/1993 | Salomon | 252/47.5 |
| 5,178,784 | 1/1993 | Salomon | 252/47.5 |
| 5,211,862 | 5/1993 | Spivack | 252/47 |

*Primary Examiner*—Jerry D. Johnson

*Attorney, Agent, or Firm*—Burgess, Ryan & Wayne

[57] ABSTRACT

The present invention relates to the preparation of antioxidant additives to lubricants and to their use in lubricating compositions. The additives according to the invention have the formula:

$$ArAr'(H)N—(R—X)_a—R'Y$$

where—Ar and Ar' are identical or different aromatic radicals, R and R', which are identical or different, denote a $C_2$-$C_{18}$ linear or branched alkylene radical, X denotes an oxygen or sulphur atom or an —NH group, a is an integer between 0 and 5 and Y is chosen from the group consisting of $—NR_1R_2$, where $R_1$ and $R_2$, which are identical or different, denote a hydrogen atom or a $C_1$-$C_{12}$ alkyl, alkenyl, cycloalkyl or arylalkyl radical $—N{=}CH—Ar_1$ where $Ar_1$ is an aryl radical containing at least one phenolic group $—NR_1—CO—Ar_1$ and

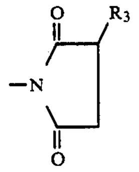

where $R_3$ denotes a saturated or unsaturated, linear or branched alkyl radical.

11 Claims, No Drawings

NITROGENOUS ADDITIVES WITH AN ANTIOXIDANT ACTION AND LUBRICATING COMPOSITIONS CONTAINING THE SAID ADDITIVES

This application is a continuation of application Ser. No. 445,392, filed Dec. 4, 1989, now abandoned.

BACKGROUND OF THE INVENTION

1. Field of the Invention

The present invention relates to the preparation of new oxidation inhibitor additives and to their use in lubricating compositions.

2. Description of the Related Art

It is known that lubricating oils, and in particular crankcase oils intended for internal combustion engines, contain various additives used to improve their performance. Some of these additives are employed to protect the oil against the oxidation caused by the high temperatures or by certain metal ions dispersed in the oil.

This degradation of the lubricant is related to the thermal and oxidative decomposition of the oil and of the additives. It gives rise to the formation and to the deposition of carbonaceous substances on the walls of the piston. If these deposits become too great, they can initiate gumming up or seizing of the piston and can increase the wear of the moving metal parts. It is therefore important to limit the degradation of the lubricants as much as possible by employing effective antioxidant additives in economically reasonable concentrations.

The protection of lubricants by means of the various organic additives is widely described. Depending on their mode of action, a distinction is generally made among these compounds between, on the one hand, free radical inhibitors (hindered phenols, aromatic amines, phenothiazines, etc.) and, on the other hand, products which decompose hydroperoxides or peroxides (metal dithiocarbamates or dithiophosphates, phosphites, thioethers, etc.).

There are also known metal deactivators which prevent the metal ions present in the oil or on the surfaces from initiating an autooxidation of the lubricant. These products act by complexing the metals.

Among all these compounds, aromatic amines and more particularly phenothiazine derivatives are the most effective, because they act according to a number of mechanisms: decomposition of the hydroperoxides, electron transfer agents, metal chelation and oxygen acceptors.

Thus, U.S. Pat. No. 2,781,318 describes the use in synthetic lubricants of alkylphenothiazines whose alkyl groups are carried by the aromatic carbons of phenothiazine.

U.S. Pat. No. 3,536,706 mentions the use of phenothiazines substituted on the aromatic nuclei by tertiary alkyl groups containing 4 to 12 carbon atoms or by aryl groups.

U.S. Pat. No. 3,803,140 suggests the use of tert-alkyl derivatives of N-alkyl- or N-alkenylphenothiazines. Nevertheless, tert-alkyl derivatives of phenothiazines which are not substituted on the nitrogen are preferred.

U.S. Pat. No. 3,344,068 describes the use of antioxidants derived from aromatic amines in ester-based synthetic lubricants. These additives may be N-alkylphenothiazines substituted by at least one alkyl group on aromatic nuclei.

U.S. Pat. No. 3,376,224 claims antioxidants derived from phenothiazine which are substituted by an alkoxymethyl group on the nitrogen atom.

WO Patent 88/02,007 describes the preparation and the use of N-alkylthioalkylphenothiazines obtained by condensation of a phenothiazine and of an alkylthioalkanol. The presence of a sulphur atom reinforces the antioxidant power of phenothiazine substituted in this manner.

SUMMARY OF THE INVENTION

We have found that the properties of antioxidant additives comprising an aromatic nitrogen could be improved by the presence of an aminoalkyl chain.

The solubility of these additives in lubricants of synthetic or mineral origin is considerably improved.

The presence of an amine functional group makes it possible to introduce other functional groups into the molecule to reinforce its antioxidant power or to impart other useful properties to it.

The antioxidant additives containing an aromatic nitrogen, according to the invention, are characterized in that they correspond to the general formula:

$$Ar-\underset{\underset{Ar'(H)}{|}}{N}-(R-X)_a-R'-Y \qquad (I)$$

where

- Ar and Ar' are identical or different aromatic radicals, it being possible for Ar' to be replaced by a hydrogen atom, or else Ar and Ar' are linked together to form an aromatic heterocyclic structure with the nitrogen to which they are attached
- R and R', which are identical or different, denote a $C_2$-$C_{18}$, preferably $C_2$-$C_6$ and advantageously $C_3$, linear or branched alkylene radical optionally substituted by a halogen or an —OH or $—NH_2$ group
- X denotes an oxygen or sulphur atom or an —NH— group
- a is an integer between 0 and 5 and preferably between 0 and 2,
- Y is chosen from the group consisting of $$-NR_1R_2 \qquad (II)$$

where $R_1$ and $R_2$, which are identical or different, denote a hydrogen atom or a $C_1$-$C_{12}$ alkyl, alkenyl, cycloalkyl or arylalkyl radical $$-N{=}CH-Ar_1 \qquad (III)$$

where $Ar_1$ is an aryl radical containing at least one phenolic group, $$-NR_1-CO-Ar_1 \text{ and} \qquad (IV)$$

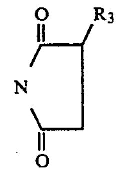

(V)

where $R_3$ denotes a hydrogen atom or a saturated or unsaturated, linear or branched alkyl radical.

DESCRIPTION OF THE PREFERRED EMBODIMENTS

The aromatic nitrogen may be an amine group linked to one or two aromatic radicals Ar and Ar'. Ar may, for example, denote a phenyl, naphthyl, anilinophenyl or phenothiazinyl radical, Ar' being replaced by a hydrogen atom. Ar and Ar' may be identical and may denote a phenyl radical.

The aromatic nitrogen may also form part of a heterocyclic ring. In this case, Ar and Ar' are linked together to form, with the nitrogen to which they are attached, an aromatic heterocyclic structure such as phenothiazine, imidazole, benzimidazole, triazole or benzotriazole. Phenothiazine derivatives are preferably employed.

Ar and Ar' may be substituted by alkyl or aryl, preferably $C_1$-$C_{12}$, radicals or by hydroxyl, alkoxy, alkylthio groups or a halogen.

$R_1$ and $R_2$ advantageously denote a hydrogen atom or a $C_1$-$C_4$ alkyl radical.

According to another feature of the invention, $R_1$ is a hydrogen atom and $R_2$ denotes an arylalkyl radical of general formula $-CH_2-Ar_1$ or $Ar_1$ has the above meaning.

The introduction of the phenolic group $Ar_1$ reinforces the antioxidant power of the additive.

The $Ar_1$ radical containing at least one phenolic OH is derived, for example, from phenol, from p-tert-butylphenol, from 2,6-di-tert-butylphenol, from 2,4-di-tert-amylphenol, from dodecylphenol, from sulphurized dodecylphenol, from catechol, from beta-naphthol or from resorcinol.

$R_3$ advantageously denotes an oligomer of a $C_2$-$C_5$ olefin, whose molecular mass is between 500 and 3,000 and preferably between 800 and 1,500.

These additives may be prepared by any known method.

For example, the additives where $Y=NR_1R_2$ are obtained by alkylating a compound containing an aromatic nitrogen. The compound containing an aromatic nitrogen is either an aromatic amine such as aniline, naphthylamine, diphenylamine, 3-aminophenothiazine or aminodiphenylamine, or a nitrogenous heterocyclic compound such as phenothiazine, imidazole, benzimidazole, triazole or benzotriazole. The use of other heterocyclic compounds may be envisaged, provided that the heterocyclic ring contains a nitrogen atom capable of being alkylated.

Acrylamide, chloroacetamide, iodoacetamide, acrylonitrile and 3-chloropropionitrile are good alkylation reactants. The alkylation reaction is followed by hydrogenation of the nitrile or amide groups.

For example, phenothiazine may be condensed with acrylonitrile under cyanoethylation conditions with a quantity of acrylonitrile which is greater than the theoretical quantity in the presence of an alkaline catalyst such as Triton B (benzyltrimethylammonium hydroxide) in methanolic solution, as described by N. L. Smith (J. Org. Chem. 15, 1129, 1950). The intermediate is then reduced to N-aminopropylphenothiazine by catalytic hydrogenation in an autoclave under hydrogen and ammonia pressure. If $a>1$, a number of successive reactions are needed.

Another method consists in reacting an epoxide, such as ethylene oxide or propylene oxide, with the aromatic nitrogen, followed by an aminolysis of the alcohol intermediate by treatment with ammonia or with an amine of general formula $R_1NHR_2$ where $R_1$ and $R_2$ have the above meaning.

It is possible, of course, to obtain compounds where $a>1$ by successive reactions with a number of molecules of epoxides or mixtures of epoxides.

If $R_2$ is an arylalkyl radical containing at least one phenolic OH, the Mannich reaction is advantageously employed for its synthesis.

The Mannich base is obtained by the reaction of a compound of general formula (I) where $Y=-NR_1R_2$ and where at least one of the groups $R_1$ or $R_2$ is a hydrogen atom, with a phenol containing at least one active hydrogen in its molecule and an aldehyde.

Linear or cyclic alkylaldehydes are employed, or else an aromatic aldehyde, but preferably formaldehyde or its derivatives such as paraformaldehyde, acetaldehyde or propionaldehyde.

Among the phenols, that chosen is generally phenol itself, p-tert-butylphenol, 2,6-di-tert-butylphenol, 2,4-di-tert-amylphenol, tert-butyl-para-cresol, dodecylphenol, sulphurized dodecylphenol, catechol, betanaphthol or resorcinol. 2,6-Di-tert-butylphenol or sulphurized dodecylphenol is advantageously employed.

The Mannich base is generally obtained by adding 0.8 to 1.5 moles, preferably 1.2 moles, of aldehyde and from 0.8 to 2.5, preferably 1, mole of compound of formula (I) to one mole of phenol.

The reaction is carried out with stirring under an inert gas atmosphere such as nitrogen, at a temperature of between 60° and 130° C. and preferably around 100° C., over a period of between 2 and 10 hours.

The operation is generally carried out in the presence of a polar solvent such as isopropanol or else an aromatic solvent such as toluene or xylenes. The water formed during the reaction is removed by azeotropic distillation.

After the reaction it suffices to remove the solvent to collect the Mannich base which can be employed directly in the lubricating compositions according to the present invention.

Compounds containing an oxaldine functional group or a Schiff base ($Y=-N=CH-Ar_1$) are obtained by reacting aldehydes of general formula $Ar_1-CHO$ with compounds of general formula (I) where $Y=NR_1R_2$ and $R_1$ and $R_2$ denote a hydrogen atom.

The compound $Ar_1-CHO$ will advantageously be salicylaldehyde, tert-butylsalicylaldehyde, 3,5-di-tert-butyl-4-hydroxybenzaldehyde or 3,5-di-tert-butyl-4-hydroxy-3-phenylpropionaldehyde.

Compounds containing an amide functional group ($Y=-NR_1-CO-Ar_1$) are obtained by reacting an acid of general formula $Ar_1-CO_2H$ with compounds of general formula (I) where $Y=NR_1R_2$ and at least one of the groups $R_1$ and $R_2$ denotes a hydrogen atom.

The compound $Ar_1-CO_2H$ will advantageously be salicylic acid, tert-butylsalicylic acid or 3,5-di-tert-butyl-4-hydroxy-3-phenylpropionic acid.

The formation of the Schiff bases or of the amides generally occurs on heating the reactants under the same operating conditions as those described for obtaining the Mannich bases.

Compounds containing an imide functional group,

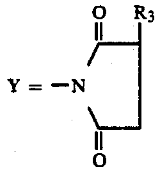

are obtained by reacting a succinic anhydride derivative with a compound of general formula (I) or $Y=NR_1R_2$ and $R_1$ and $R_2$ denote a hydrogen atom.

The introduction of the imide functional group into the molecule imparts dispersant properties to the additives according to the invention.

The succinic anhydride employed is generally substituted by an alkyl group, preferably an oligomer.

The oligomer originates from the oligomerization of a $C_2$–$C_5$ olefin. It has a molecular mass of between 500 and 3,000, and preferably between 800 and 1,500. The oligomer contains a residual unsaturation and reacts with maleic anhydride to give the substituted succinic anhydride.

The operation is generally carried out by condensing 0.5 to 1.5 moles, preferably 1 mole, of compound of formula (I) per mole of anhydride in an organic solvent such as toluene or xylenes, capable of removing the water formed during the reaction by azeotropic distillation. The reaction gives rise to the formation of amide and imide functional groups.

After the reaction it suffices to remove the solvent to collect the additive which can be employed in the lubricating compositions of the invention.

The additive may be incorporated into natural or synthetic lubricating oils or into mixtures of such oils. By way of example there may be mentioned ordinary or refined mineral oils of paraffinic or naphthenic composition, and hydrorefined oils. Synthetic oils, such as polybutenes, alkylbenzenes such as dinonylbenzenes and tetradecylbenzene, polypropylene glycol ethers or esters, esters of polycarboxylic acids such as methyl adipate and pentaerythritol heptanoate, silicone oils such as polysiloxanes, complete or partial esters of phosphoric acid, especially tricresyl phosphate, and alkylphosphoric acids and 1.96 g (0.01 mole) of 2,6-di-tert-butylphenol and 100 ml of ethanol are introduced with stirring into a 250-ml reactor. Stirring is continued for 10 minutes at ambient temperature and 0.33 g (0.011 moles) of paraformaldehyde are then added. The mixture is refluxed for 24 hours and is then left at ambient temperature for another 96 hours. The solid is separated off by filtration, washed with ethanol and dried in an oven at 100° C. (m=2.31 g, Yld 51%).

EXAMPLE III

Mannich base with sulphurized dodecylphenol a) 141.5 g of $S_2Cl_2$ are introduced with stirring, under a nitrogen atmosphere and while the temperature is maintained between 20° and 30° C., over approximately one hour, into a reactor containing 550 g of dodecylphenol. After the addition has been completed, the mixture is heated for 1 hour at 150° C., then 1 hour at 180° C. and 1 hour at 200° C. while a stream of nitrogen is maintained to remove the hydrogen chloride. Cooling is then allowed to take place with stirring, while a gentle stream of nitrogen is maintained. (The product obtained has a sulphur content of 10.3%).

b) 2.56 g (0.01 mole) of N-aminopropylphenothiazine, 2.93 g (0.005 moles) of sulphurized dodecylphenol (IIIa) and 200 ml of ethanol are introduced with stirring into a 250-ml reactor. Stirring is continued for 5 minutes at ambient temperature and 0.33 g of paraformaldehyde are then added and the mixture is refluxed for 8 h.

The water formed is removed with the solvent as it is formed. The mixture is then allowed to cool. After 2 days at ambient temperature, the precipitate obtained is filtered off and is then dissolved in dichloromethane. After filtration and removal of the solvent, 1.3 g of a chestnut-brown powder are collected.

The presence of the absorption band of the nitrogen doublet at 3300 $cm^{-1}$, characteristic of the expected product, is verified by IR spectroscopy.

EXAMPLE IV 16.7 g (0.1 mole) of naphthylamine are heated under reflux with stirring with 4.09 g of sodium amide in 200 ml of toluene. After one hour 12.1 g of 3-dimethylamino-1-chloropropane are added dropwise and heating under reflux is continued for another 4 hours. After cooling, the mixture is washed with water and the toluene solution is dried over magnesium sulphate. After evaporation of the solvent, a yellow oil consisting chiefly of (N,N-dimethyl-3-aminopropyl)naphthylamine is collected.

EXAMPLE V 20 g (0.1 mole) of phenothiazine and 4.1 g of sodium amide are heated under reflux with stirring in 200 ml of toluene. After one hour this solution, cooled beforehand, is poured into 250 ml of 1,2-di(2-chloroethoxy)ethane. The mixture is heated under reflux for 4 hours. The toluene and the excess 1,2-di(2-chloroethoxy)ethane are evaporated off.

The residue is taken up with 200 ml of a 30% strength aqueous ammonia solution and 100 ml of methanol and the whole is kept at 60° C. for 72 hours. The alcohol is removed and the product is extracted with two 150-ml portions of toluene. The organic phase is washed with two 50-ml portions of water and is dried over magnesium sulphate. After evaporation of the solvent, a product consisting chiefly of 2- (2-aminoethoxy) (2-phenothiazinylethoxy)ethane is recovered.

EXAMPLE VI

The oxidation stability of lubricating compositions containing an additive of the invention is evaluated in this example. The tests are carried out at 160° C. using a bomb pressurized with oxygen in the presence of a metal catalyst, a combustion catalyst and water so as partly to simulate the conditions to which the oil may be subjected in a petrol engine.

The metal catalyst is a mixture of soluble Pb, Cu, Fe, Mn and Sn naphthenates.

The oxidation stability of the lubricants is assessed by measuring the induction time, that is to say the time interval between the beginning of the test and the rapid drop in pressure in the bomb.

The longer this induction time, the more effective are the antioxidant additives forming part of the lubricant composition.

TABLE I

| | Induction time |
|---|---|
| Reference lubricant = A | 113 |
| A + 0.3% Example I additive | 131 |

TABLE I-continued

| | Induction time |
|---|---|
| A + 0.5% Example I additive | 185 |
| A + 0.5% Example II additive | 140 |
| A + 1% Example II additive | 172 |
| A + 1% Example III additive | 168 |
| A + 0.5% Example IV additive | 136 |
| A + 0.5% Example V additive | 137 |

A = ELF 15 W 30 grade lubricant without an antioxidant additive of aromatic amine type.

We claim:

1. An additive for lubricating oil with an antioxidant action, comprising an aromatic nitrogen compound selected from the group consisting of:

(1) 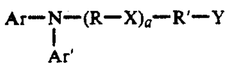 (I)

wherein Ar and Ar' are linked together to form a phenothiazine structure with the nitrogen to which they are attached, and wherein said structure can be substituted by hydroxyl, halogen or $C_1$–$C_{12}$ alkyl, aryl, alkoxy or alkylthio;

R and R', which are identical or different, represent a $C_2$–$C_{18}$ linear or branched alkylene radical optionally substituted by a halogen or an —OH or —$NH_2$ group;

X represents an —NH— group, a is an integer between 0 and 5 and Y is selected from the group consisting of $$-NR_1R_2 \qquad (II)$$

wherein $R_1$ and $R_2$ represent a hydrogen atom, $$-N{=}CH-Ar_1 \qquad (III)$$

wherein $Ar_1$ is an aryl radical containing at least one phenolic group, $$-NR_1-CO-Ar_1 \qquad (IV)$$

and

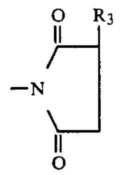 (V)

wherein $R_3$ represents a hydrogen atom or a saturated or unsaturated, linear or branched alkyl radical; and $R_1$ and $Ar_1$ are as indicated, (2) 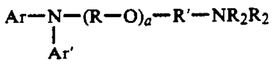

wherein Ar, Ar', R, R' and a are as indicated and $R_1$ and $R_2$ are different and represent a hydrogen atom or a $C_2$–$C_{12}$, cycloalkyl or arylalkyl radical; and (3) 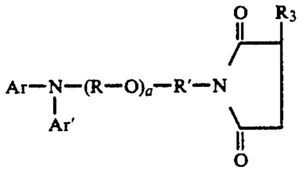

wherein Ar, Ar', $R_3$ and a are as indicated and R and R', which are identical or different, represent a $C_2$–$C_{18}$ linear or branched alkylene radical substituted by a halogen or an —OH or —$NH_2$ group.

2. An additive according to claim 1 wherein R and R' represent a $C_2$–$C_4$ linear or branched chain alkylene radical.

3. Additives according to claim 1 wherein a is an integer between 0 and 2.

4. Additives according to claim 1 wherein $R_3$ is an oligomer of a $C_2$–$C_5$ olefin whose molecular weight is between 500 and 3,000.

5. Additives according to claim 1 wherein $R_3$ is an oligomer of a $C_2$–$C_5$ olefin whose molecular weight is between 800 and 1,500.

6. A lubricating composition comprised of a natural or synthetic lubricating oil and 0.01 to 10 percent by weight of an additive of claim 1.

7. The lubricating composition of claim 6 wherein R and R' represent a $C_2$–$C_6$ linear or branched chain alkylene radical.

8. The lubricating composition of claim 6 wherein a is an integer between 0 and 2.

9. The lubricating composition of claim 6 wherein $R_3$ is an oligomer of a $C_2$–$C_5$ olefin whose molecular weight is between 500 and 3,000.

10. The lubricating composition of claim 6 wherein $R_3$ is an oligomer of a $C_2$–$C_5$ olefin whose molecular weight is between 800 and 1,500.

11. The lubricating composition of claim 6 which contains a further additive selected from corrosion inhibitors, detergents, antiwear dispersants and antifoam additives.

* * * * *